US010375467B2

(12) United States Patent
Xu et al.

(10) Patent No.: US 10,375,467 B2
(45) Date of Patent: Aug. 6, 2019

(54) SYSTEMS, APPARATUS, AND METHODS FOR HEARING PROTECTION

(71) Applicant: Massachusetts Institute of Technology, Cambridge, MA (US)

(72) Inventors: Jun Xu, Medford, MA (US); Nicholas Fang, Lexington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 15/870,372

(22) Filed: Jan. 12, 2018

(65) Prior Publication Data

US 2018/0160217 A1 Jun. 7, 2018

Related U.S. Application Data

(63) Continuation of application No. PCT/US2016/031632, filed on May 10, 2016.
(Continued)

(51) Int. Cl.
*A61F 11/08* (2006.01)
*H04R 3/04* (2006.01)
(Continued)

(52) U.S. Cl.
CPC ............ *H04R 1/1083* (2013.01); *A61F 11/08* (2013.01); *G10K 11/162* (2013.01);
(Continued)

(58) Field of Classification Search
CPC .. A61F 11/08; A61F 2011/085; G10K 11/162; H04R 1/1016; H04R 1/1083; H04R 3/04
(Continued)

(56) References Cited

U.S. PATENT DOCUMENTS

2006/0042867 A1 3/2006 Haussmann et al.
2010/0012586 A1 1/2010 Angelescu et al.
(Continued)

OTHER PUBLICATIONS

International Search Report and Written Opinion dated Aug. 5, 2016 for International Application No. PCT/US2016/031632, 13 pages.

*Primary Examiner* — Vivian C Chin
*Assistant Examiner* — Friedrich Fahnert
(74) *Attorney, Agent, or Firm* — Smith Baluch LLP

(57) ABSTRACT

Systems, apparatus, and methods for filtering acoustic energy include a first conduit substantially aligned with a longitudinal axis and defining a first opening for receiving incident acoustic energy from the environment. A cavity in fluid communication with the first conduit selectively amplifies and/or dampens the acoustic energy based on an associated resonance frequency. A moving element disposed in the cavity may be displaced relative to the cavity in a direction substantially aligned with the longitudinal axis and in an amount related to a sound pressure level of acoustic energy in the cavity. A second conduit substantially aligned with the longitudinal axis and in fluid communication with the cavity selectively attenuates acoustic energy from the cavity based on the sound pressure level by receiving at least some of the acoustic energy from the cavity and/or the moving element when it is displaced from the cavity.

23 Claims, 10 Drawing Sheets

Related U.S. Application Data

(60) Provisional application No. 62/192,124, filed on Jul. 14, 2015.

(51) Int. Cl.
   *G10K 11/162* (2006.01)
   *H04R 1/10* (2006.01)

(52) U.S. Cl.
   CPC ............ *H04R 1/1016* (2013.01); *H04R 3/04* (2013.01); *A61F 2011/085* (2013.01)

(58) Field of Classification Search
   USPC .......................... 381/72, 322, 328, 380, 382; 128/864–868; 180/130, 135; 181/135; 2/423
   See application file for complete search history.

(56) References Cited

U.S. PATENT DOCUMENTS

| | | | |
|---|---|---|---|
| 2012/0305329 A1 | 12/2012 | Keady et al. | |
| 2013/0126262 A1 | 5/2013 | Wilmink et al. | |
| 2014/0373854 A1* | 12/2014 | Keady | A61F 11/10 128/865 |
| 2016/0295311 A1* | 10/2016 | Keady | H04R 25/652 |
| 2017/0295438 A1* | 10/2017 | De Haan | H04R 25/505 |

\* cited by examiner

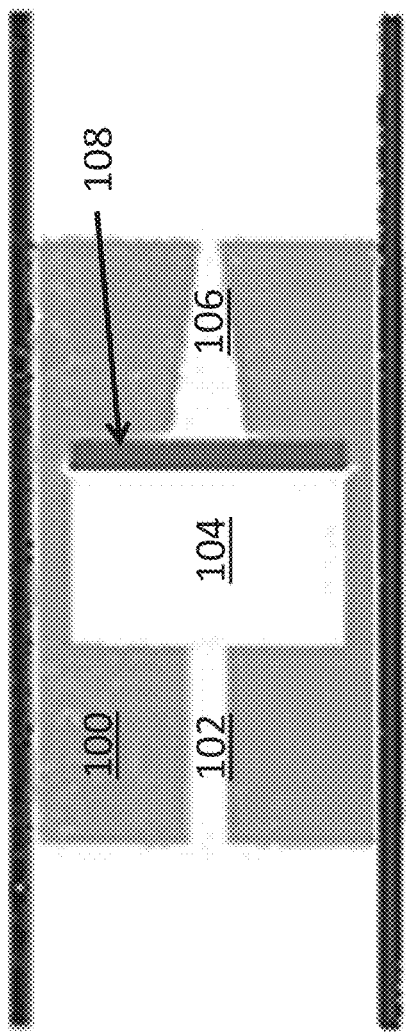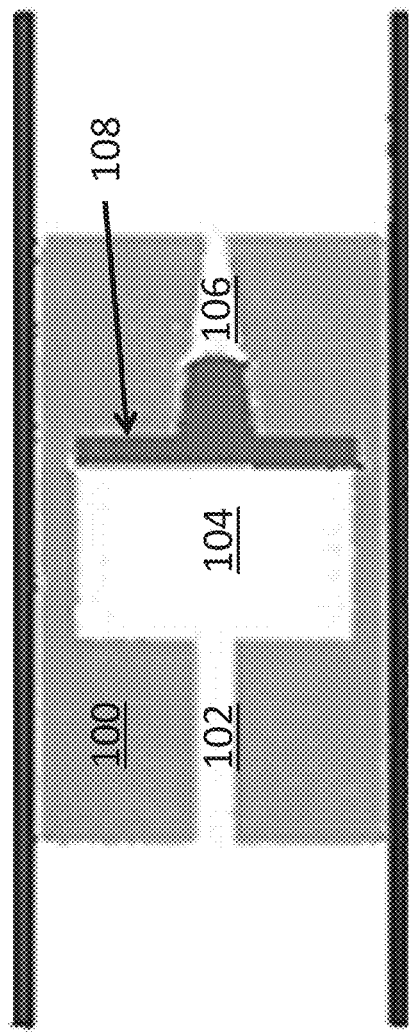

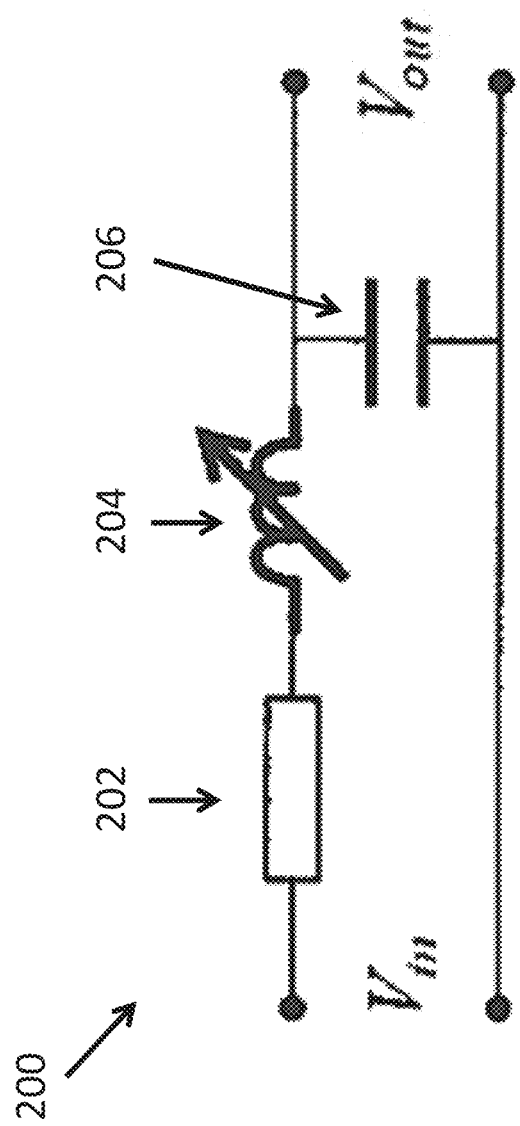

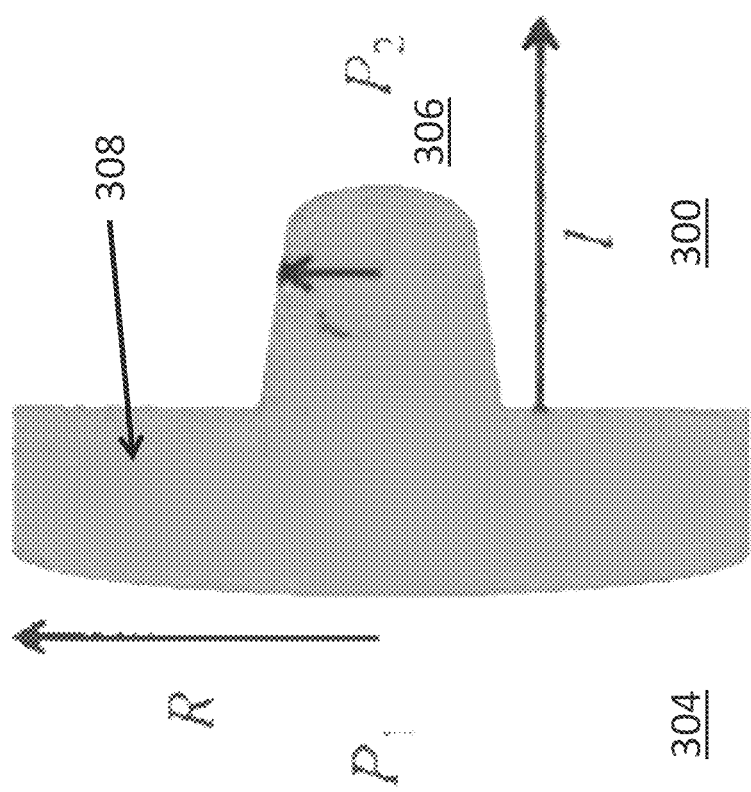

SYSTEMS, APPARATUS, AND METHODS FOR HEARING PROTECTION

CROSS-REFERENCE TO RELATED APPLICATIONS

This application is a bypass continuation application of International Application No. PCT/US2016/031632, filed May 10, 2016, and entitled "Systems, Apparatus, and Methods for Hearing Protection," which in turn claims the priority benefit, under 35 U.S.C. 119(e), of U.S. Application No. 62/192,124, filed on Jul. 14, 2015, and entitled "Sound Pressure Level Sensitive Passive Hearing Protector by Acoustic Metamaterials." Each of these applications is incorporated herein by reference in its entirety.

GOVERNMENT SUPPORT STATEMENT

This invention was made with Government support under Contract No. W31P4Q-12-C-0158 awarded by the Defense Advanced Research Projects Agency. The Government has certain rights in the invention.

TECHNICAL FIELD

The present disclosure relates generally to systems, apparatus, and methods for selectively filtering sound pressure. More specifically, the present disclosure relates to systems, apparatus, and methods for hearing protection.

BACKGROUND

Without protection devices, exposure to high intensity noises may lead to temporary and/or permanent damage or hearing loss. Conventional passive hearing protection devices, such as inexpensive foam ear plugs, have been widely used since the end of World War II. These passive hearing protection devices attenuate the incident acoustic energy across all frequencies of sound at a fixed ratio.

Active noise reduction or active noise control devices incorporate noise-canceling circuitry to reduce unwanted sound by the addition of a second sound designed to cancel the first. These active hearing protection devices sense incoming acoustic waves, generate new acoustic waves with the same amplitude as—but the inverted phase of—the original acoustic waves, and emit the new acoustic waves for destructive interference with the original acoustic waves.

SUMMARY

Existing passive hearing protection devices degrade operational capabilities by attenuating the incident acoustic energy across all frequencies of sound at a fixed ratio. Meanwhile, active hearing protection devices are relatively expensive, complex, bulky, and heavy. Furthermore, the active circuitry requires continuous power supply for operation, thus limiting the applications available for active sound protection devices.

The present disclosure introduces new systems, apparatus, and methods for selectively filtering sound pressure, including new passive hearing protection devices. In some embodiments, an acoustic metamaterial may be used to attenuate incoming acoustic pressure waves in certain frequency ranges. Some embodiments feature sensitivity to incoming sound pressure levels. For example, the transmission coefficient of acoustic energy passing through a passive hearing protection device may decrease when the incoming sound pressure level increases, thereby providing more protection in high noise environments, such as military operation locations, factories, construction sites, airports, and music performance venues. This feature cannot be realized in conventional passive hearing protection devices.

Due to the enhanced interaction of acoustic waves and acoustic metamaterials, embodiments may be relatively inexpensive, simple, compact (e.g., as small as a few centimeters), and light (e.g., about ten grams). Furthermore, some embodiments do not require additional power supply for operation.

According to some embodiments, a hearing protection device has an outer shape and size for inserting at least a portion of the device in a human ear canal. The outer shape defines a first opening for receiving incident acoustic energy from an environment and a second opening positioned opposite to the first opening for transmitting filtered acoustic energy into the ear canal. The device has a longitudinal axis extending from the first opening to the second opening. The device also includes a first conduit extending inward from the first opening and a cavity in fluid communication with the first conduit for selectively amplifying and/or dampening the acoustic energy based on a resonance frequency of the cavity. The cavity includes a mesh element disposed in a plane substantially normal to the longitudinal axis. The mesh element divides the cavity into a proximal compartment for receiving the acoustic energy from the first conduit and a distal compartment. The cavity further includes liquid disposed in the distal compartment. The liquid is displaceable relative to the device in a direction substantially aligned with the longitudinal axis and in an amount related to a sound pressure level of acoustic energy in the cavity. A second conduit in fluid communication with the distal compartment and extending outward to the second opening selectively attenuates acoustic energy from the cavity based on the sound pressure level by receiving at least a portion of at least one of the acoustic energy from the cavity and, when displaced from the distal compartment, the liquid.

The device may be configured to be combined with an ear plug. The outer shape may include at least one of a domed flange, a bell-shape, and a bullet-shape. The device may include at least one of a foam, a silicone, and a thermoplastic. The device may be manufactured using at least one of additive manufacturing, rotational plastic molding, injection molding, blow molding, extrusion molding, and thermoforming. The device may have an outer radius from about 5 mm to about 7 mm and an outer length from about 10 mm to about 14 mm.

The mesh element may include at least one of a foam and a metal. The mesh element may have a thickness from about 0.2 mm to about 0.5 mm. The mesh element may have a pore size from about 0.1 mm to about 0.2 mm. The mesh element may maintain the liquid at a particular position in the cavity. The mesh element and the liquid may form a liquid membrane. The liquid may form a meniscus in each of a plurality of pores of the mesh element for a plurality of menisci. In some embodiments, a cascade of mesh elements may be disposed in a plurality of parallel planes, each plane of the plurality of planes being substantially normal to the longitudinal axis, such that the cascade of mesh elements divide the cavity into more than two compartments. Liquid may be disposed in at least one intermediate compartment between a first mesh element and a second mesh element of the cascade of mesh elements such that the liquid forms a meniscus in each of a plurality of pores of the first mesh element and each of a plurality of pores of the second mesh element.

The position of the liquid may be based at least in part on at least one of an acoustic pressure field difference between the cavity and the second conduit and a surface tension between the liquid and at least one of the mesh element, air, an inner surface of the cavity, and an inner surface of the second conduit. At least one of the mesh element, the inner surface of the cavity, and the inner surface of the second conduit may be treated to control the surface tension. At least one of a shape, an angle, and a texture of the inner surface of the second conduit may be selected to modify the acoustic pressure field difference between the cavity and the second conduit.

A length of the second conduit may be selected to modify frequencies transmitted of the filtered acoustic energy. The length of the second conduit may be selected to allow transmission of frequencies from about 50 Hz to about 4,000 Hz and, in some embodiments, from about 100 Hz to about 800 Hz.

According to some embodiments, a method for protecting hearing of a listener in an environment includes inserting at least a portion of a device in a human ear canal, the device having an outer shape defining a first opening for receiving incident acoustic energy from the environment and a second opening positioned opposite to the first opening for transmitting filtered acoustic energy into the ear canal, the device having a longitudinal axis extending from the first opening to the second opening. The method also includes receiving incident acoustic energy from the environment via the first opening in the device, a first conduit extending inward from the first opening, and selectively amplifying and/or dampening the acoustic energy via a cavity in fluid communication with the first conduit based on a resonance frequency of the cavity. The cavity includes a mesh element disposed in a plane substantially normal to the longitudinal axis, the mesh element dividing the cavity into a proximal compartment for receiving the acoustic energy from the first conduit and a distal compartment. The method further includes selectively attenuating, based on a sound pressure level of acoustic energy in the cavity, acoustic energy from the cavity via liquid disposed in the distal compartment and a second conduit in fluid communication with the distal compartment and extending outward to the second opening, the liquid displaceable relative to the device in a direction substantially aligned with the longitudinal axis and in an amount related to the sound pressure level of the acoustic energy in the cavity, the second conduit receiving at least a portion of at least one of the acoustic energy from the cavity and, when displaced from the distal compartment, the liquid. The method includes transmitting the filtered acoustic energy via the second opening of the second conduit positioned opposite to the first opening along the longitudinal axis.

According to some embodiments, an apparatus for filtering acoustic energy in an environment includes a first conduit substantially aligned with a longitudinal axis, the first conduit defining a first opening for receiving incident acoustic energy from the environment, and a cavity in fluid communication with the first conduit, the cavity for selectively amplifying and/or dampening the acoustic energy based on a resonance frequency of the cavity. The cavity includes a moving element disposed in the cavity, the moving element displaceable relative to the apparatus in a direction substantially aligned with the longitudinal axis and in an amount related to a sound pressure level of acoustic energy in the cavity. The apparatus also includes a second conduit substantially aligned with the longitudinal axis and in fluid communication with the cavity for selectively attenuating acoustic energy from the cavity based on the sound pressure level by receiving at least a portion of at least one of the acoustic energy from the cavity and, when displaced from the cavity, the moving element, the second conduit defining a second opening positioned opposite to the first opening along the longitudinal axis for transmitting filtered acoustic energy.

The cavity further may include a mesh element disposed in a plane substantially normal to the longitudinal axis, the mesh element dividing the cavity into a proximal compartment for receiving the acoustic energy from the first conduit and a distal compartment such that the moving element is disposed in the distal compartment and the second conduit is in fluid communication with the distal compartment.

Dimensions of at least one of the first conduit, the cavity, and the second conduit may be selected for tuning the resonance frequency. The resonance frequency may be from about 1.5 kHz to about 4.0 kHz.

At least one of the first conduit and the second conduit may be substantially at least one of cylindrical, helical, and conical. The second conduit may have a conical shape that tapers toward the second opening. The second opening may include a plurality of parallel openings and the second conduit may include a plurality of parallel conduits. The plurality of parallel openings and the plurality of parallel conduits may be arranged in a pattern selected to decrease insertion loss. The cavity may be substantially at least one of cylindrical and spherical. The cavity may be a Helmholtz-type resonator.

The moving element may be at least one of a fluid and a solid. For example, the moving element may be a water droplet. The moving element may have a thickness from about 2 mm to about 3 mm and/or a volume from about 100.5 mm$^3$ to about 150.8 mm$^3$. The position of the moving element may be based at least in part on an acoustic pressure field difference between the cavity and the second conduit.

According to some embodiments, a method for filtering acoustic energy in an environment includes receiving incident acoustic energy from the environment via an opening of a first conduit substantially aligned with a longitudinal axis and selectively amplifying and/or dampening the acoustic energy via a cavity in fluid communication with the first conduit based on a resonance frequency of the cavity. The method also includes selectively attenuating, based on a sound pressure level of acoustic energy in the cavity, acoustic energy from the cavity via a moving element disposed in the cavity and a second conduit substantially aligned with the longitudinal axis and in fluid communication with the cavity, the moving element displaceable relative to the second conduit in a direction substantially aligned with the longitudinal axis and in an amount related to the sound pressure level of the acoustic energy in the cavity, the second conduit receiving at least a portion of at least one of the acoustic energy from the cavity and, when displaced from the cavity, the moving element. The method further includes transmitting filtered acoustic energy via a second opening defined by the second conduit and positioned opposite to the first opening along the longitudinal axis.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 1A-1B are schematic views illustrating a design strategy for a hearing protection device in accordance with some embodiments.

FIG. 2 is a circuit diagram representing an analogous design strategy for a hearing protection device, in which the effective inductance is the function of the applied voltage, in accordance with some embodiments.

FIG. 3 is a schematic view illustrating fluid in a tapered channel of a hearing protection device in accordance with some embodiments.

DETAILED DESCRIPTION

Figure 4:
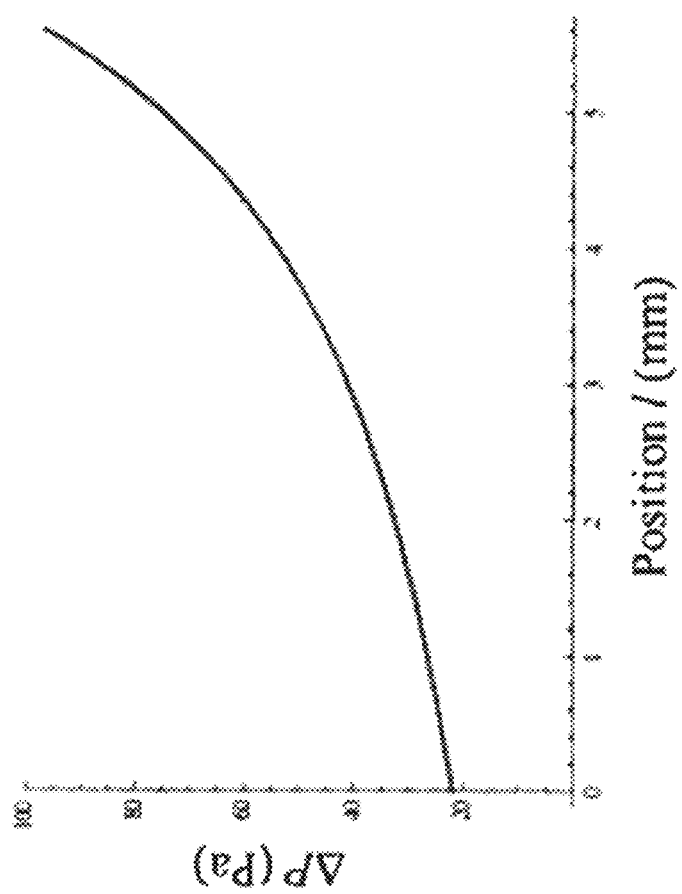
FIG. 4 is a plot illustrating the calculated pressure field difference as a function of the fluid front end position in accordance with some embodiments.

The present disclosure introduces new systems, apparatus, and methods for selectively filtering sound pressure, including new passive hearing protection devices. In some embodiments, an acoustic metamaterial may be used to attenuate incoming acoustic pressure waves in certain frequency ranges. Some embodiments feature sensitivity to incoming sound pressure levels. For example, the transmission coefficient of acoustic energy passing through a passive hearing protection device may decrease when the incoming sound pressure level increases, thereby providing more protection to individuals exposed to excessively noisy devices and/or environments (e.g., more than 80 dB). This feature is cannot be realized in conventional passive hearing protection devices.

According to some embodiments, a design strategy is based on a close analogy between the propagation of sound in tubes and/or chambers and electronic circuits. When the dimensions of the region in which the sound propagates are much smaller than the wavelength, a lumped-parameter model is appropriate.

By considering the pressure and velocity of the fluid inside a tube with a rigid wall, an open end of the tube may be considered analogous to an acoustic inductor with effective inductance $L_A$ as follows:

$$L_A = j\omega \frac{\rho_0 l}{s}, \quad (1)$$

where j is the imaginary unit, $\omega$ is the angular frequency ($\omega=2\pi f$), $\rho_0$ is the density of the medium in the tube, l is the length of the tube, and s is the cross-sectional area of the tube.

A rigid end of the tube may be considered analogous to an acoustic capacitor with effective capacitance $C_A$ as follows:

$$C_A = \frac{V}{\rho_0 c_0^2}, \quad (2)$$

where v is the volume of the cavity, $\rho_0$ is the density of the medium in the tube, and $c_0$ is the velocity of sound in the medium.

A Helmholtz resonator is a rigid container of a known volume with a first opening to receive sound waves, a cavity or chamber (e.g., substantially spherical), and a second opening that is narrow and/or tapered (e.g., funnel shaped). The second opening may be intended to be inserted in a human ear canal to enhance sound of a particular frequency to which the resonator is tuned. Upon receipt of a sound wave of a particular frequency at the first opening, the sound wave will be reinforced by the phenomenon of air resonance in the cavity. Meanwhile, sound waves of other frequencies will be dampened.

A Helmholtz resonator may be considered a series of inductors and capacitors. Fluid inside the cavity of the Helmholtz resonator is much easier to compress than fluid in the narrow and/or tapered second opening, indicating that higher acoustic energy density is distributed in the narrow and/or tapered second opening. Moreover, the pressure gradient along the first opening is much greater than that inside the cavity. Therefore, the cavity displays acoustic capacitance, and the narrow and/or tapered second opening displays acoustic inductance.

Inspired by a traditional bandpass filter in electronic circuitry, acoustic components may be assembled to form an acoustic wave bandpass filter. For example, the resonance frequency of the filter may be tuned by changing one or more geometric parameters (e.g., the volume, length, and/or the cross sectional area of the first opening, cavity, and/or second opening) of a Helmholtz resonator. As an acoustic metamaterial, a Helmholtz-type resonator may squeeze an acoustic wave into a sub-wavelength region, allowing for a more compact device size. However, the transmission coefficient of a Helmholtz resonator, working as an acoustic bandpass filter, is not sensitive to incoming sound pressure levels.

In some embodiments, a moving element that responds to the incoming acoustic pressure field is included in a Helmholtz-type resonator. For example, the moving element may be fluid (e.g., a droplet of liquid), such as water, and/or a solid material, such as a soft rubber. The moving element may be selected based on the desired sensitivity. For example, solid materials have a higher modulus and lower sensitivity. Instead of, or in addition to, mechanical deformation, which can dramatically reduce the force for the movement, the moving element may rely on surface tension between a fluid and a solid. Pressure differences and surface tension may be balanced by modifying the shape and angle of the narrow and/or tapered second opening in a Helmholtz resonator, thereby controlling the front end position of the moving element. A goniometer, for example, may be used to measure the contact angle between a liquid and solid to determine the surface tension. Thus, by introducing a moving element, the device may have sound pressure level sensitive features.

FIGS. 1A-1B are cross-sectional schematic views illustrating the above design strategy for a hearing protection device 100 in accordance with some embodiments. The Helmholtz resonator-type device 100 defines a first opening 102, cavity 104, tapered second opening 106, and a moving element (i.e., fluid) 108 that has been disposed (e.g., injected) in the cavity 104. In FIG. 1A, device 100 is exposed to a low pressure incident sound. The moving element 108 remains in cavity 104. In FIG. 1B, the device 100 is exposed to a high pressure incident sound, and a portion of the moving element 108 enters a proximal portion of the tapered second opening 106.

According to some embodiments, a hearing protection device may be considered analogous to a circuit with voltage output $V_{out}$ as follows:

$$V_{out} = \frac{1}{1 - \omega^2 L(V_{in})C + jRC\omega} V_{in}, \quad (3)$$

where $\omega$ is the angular frequency ($\omega=2\pi f$), effective inductance L is a function of the applied voltage $V_{in}$, C is the effective capacitance, j is the imaginary unit, and R is the effective resistance.

FIG. 2 is a circuit diagram representing an electronic circuit 200 analogous to the above design strategy in accordance with some embodiments. In FIG. 2, voltage $V_{in}$ is applied to the circuit 200, which includes a resistor 202 to reduce the flow of energy, a variable inductor 204 to store energy, and a capacitor 206 to store energy.

FIG. 3 is cross-sectional schematic view illustrating a portion of a hearing protection device 300 in accordance with some embodiments. In FIG. 3, the device 300 includes a cylindrical cavity 304 and a tapered second opening 306, in which fluid 308 is at an equilibrium state in accordance with some embodiments. According to some embodiments, the acoustic pressure field difference $\Delta P$ between the cavity 304 and the second opening may be modeled as follows:

$$\Delta P = P_1 - P_2 = \frac{2\gamma_{la}\cos\theta}{R} - \frac{2\gamma_{la}\cos\theta}{r} \quad (4)$$

where $P_1$ is the pressure in the cavity 304, $P_2$ is the pressure in the tapered second opening 306, $\gamma_{la}$ is the surface tension between the fluid 308 and air, $\theta$ is the contact angle between the fluid 308 and the inner wall of the device 300, R is the radius of the cavity 304, and r is a radius of the tapered second opening 306.

Due to the tapered shape of the second opening 306, r is a function of the position along the length l of the second opening. Higher pressure in the cavity 304 will cause more fluid 308 to enter the second opening 306, leading to larger acoustic energy attenuation. Once an incoming pressure field disappears, the fluid 308 will be pulled back into the cavity 304.

FIG. 4 is a plot illustrating the calculated acoustic pressure field difference as a function of the fluid front end position in accordance with some embodiments. The acoustic pressure field difference $\Delta P$ increases exponentially as the position of the fluid is shifted further along the length l of the second opening.

Figure 5:
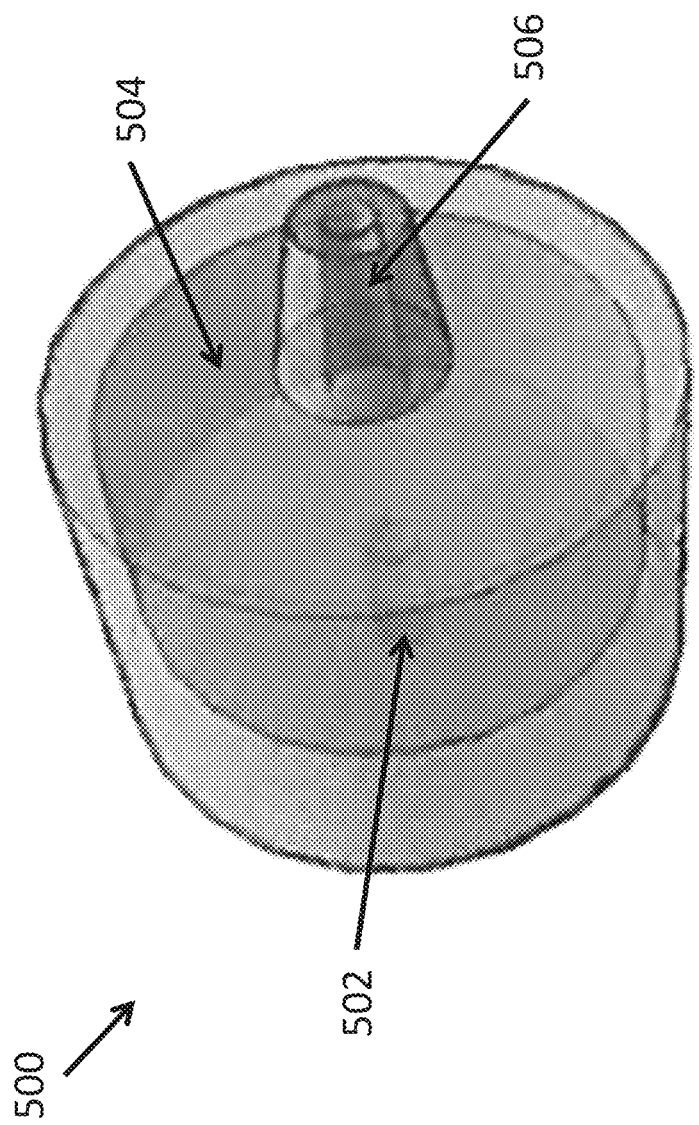
FIG. 5 is a perspective view of a hearing protection device in accordance with some embodiments.

FIG. 5 is a three-dimensional wireframe perspective view of a hearing protection device 500 in accordance with some embodiments. In FIG. 5, the device 500 defines a first tube opening 502, a cylindrical cavity 504, and a second tube opening 506, wherein the second tube opening 506 tapers in the direction distal to the cavity 504.

Figure 6:
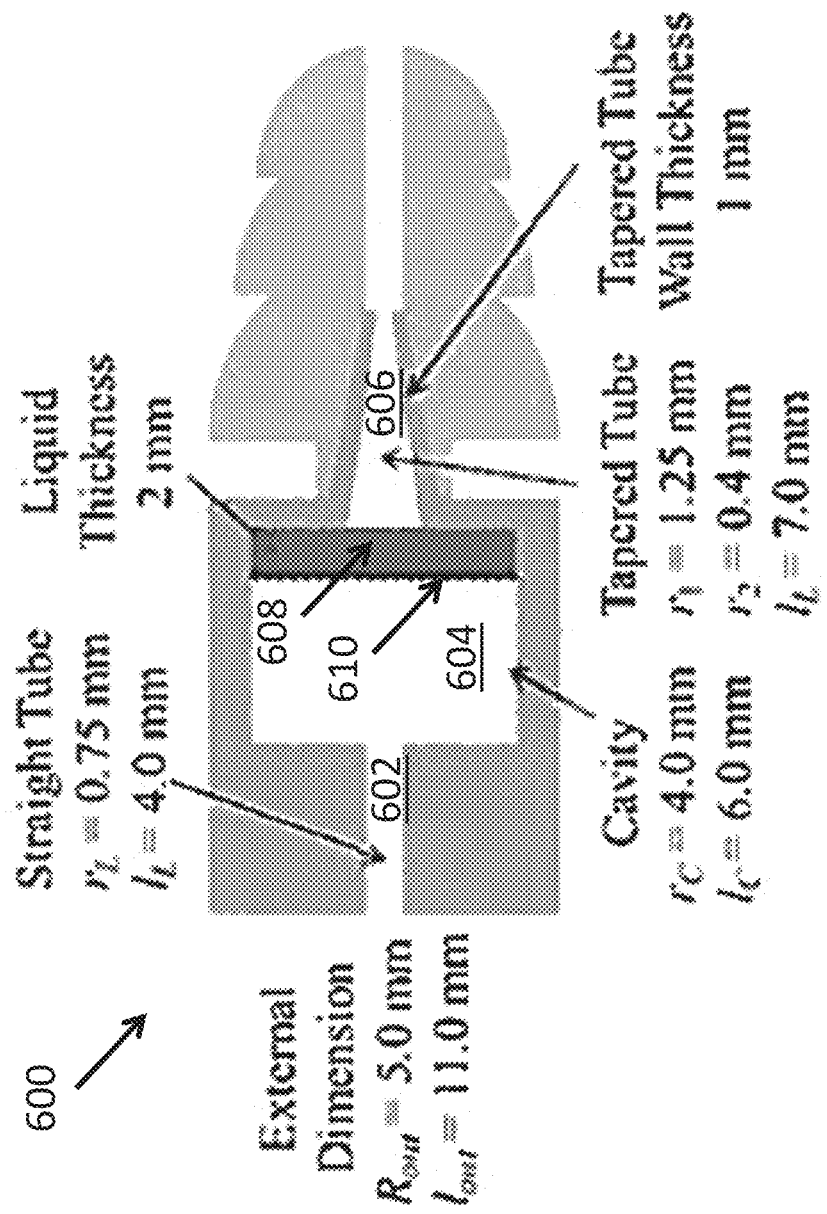
FIG. 6 is a cross-sectional view of a hearing protection device in accordance with some embodiments.

FIG. 6 is a cross-sectional schematic view of a hearing protection device 600 in accordance with some embodiments. The resonance frequency of device 600 is set at 2 kHz. According to some embodiments, the resonance frequency of a device may range from about 1.5 kHz to about 4.0 kHz, including, but not limited to, about 1.5 kHz, 1.6 kHz, 1.7 kHz, 1.8 kHz, 1.9 kHz, 2 kHz, 2.1 kHz, 2.2 kHz, 2.3 kHz, 2.4 kHz, 2.5 kHz, 2.6 kHz, 2.7 kHz, 2.8 kHz, 2.9 kHz, 3.0 kHz, 3.1 kHz, 3.2 kHz, 3.3 kHz, 3.4 kHz, 3.5 kHz, 3.6 kHz, 3.7 kHz, 3.8 kHz, 3.9 kHz, and 4.0 kHz.

The outer surface of the device 600 may be similar to a conventional ear plug or designed to be inserted into or combined with an ear plug, such that the device includes or is connected to, for example, domed flanges or other shapes for maintaining position in and/or seal against a user's outer ear and/or ear canal. The device may come in different shapes (e.g., bell or bullet) and/or sizes to accommodate different users. In some embodiments, the device may be custom-shaped or molded to fit an individual user for a particular activity.

Device 600 is fabricated by a three-dimensional (3D) printer using high stiffness resin. According to some embodiments, a device or a portion or surface thereof may comprise foam, silicone, a thermoplastic, and/or another material. A device may be manufactured as one or more components using one or more of additive manufacturing, rotational plastic molding, injection molding, blow molding, extrusion molding, thermoforming, and/or other manufacturing techniques. In some embodiments, the moving element (e.g., a fluid droplet) is disposed in a device (e.g., inserted or injected) during assembly of the device. In other embodiments, the moving element (e.g., a fluid droplet) is disposed in a device (e.g., inserted or injected) after device assembly but prior to use of the device.

In FIG. 6, device 600 has external dimensions, including an outer radius Rout of 5.0 mm and an outer length $L_{out}$ of 11.0 mm. According to some embodiments, the outer radius of a device may range from about 5 mm to about 7 mm, and the outer length of a device may range from about 10 mm to about 14 mm.

In FIG. 6, device 600 defines a first tube opening 602 with a radius $r_L$ of 0.75 mm and a length $l_L$ of 4.0 mm. According to some embodiments, the dimensions of the tube are selected for tuning the resonance frequency. In order to satisfy with the acoustic wave behavior in Helmholtz resonator, the range of the geometric parameters should be within about 10%.

In FIG. 6, device 600 defines a cylindrical cavity 604 with a radius $r_C$ of 4.0 mm and a length $l_C$ of 6.0 mm for a volume of about 301.6 mm$^3$. According to some embodiments, the dimensions of the cavity are selected for tuning the resonance frequency. In order to satisfy with the acoustic wave behavior in Helmholtz resonator, the range of the geometric parameters should be within about 10%.

In FIG. 6, device 600 defines a tapered second tube opening 606 with a first radius $r_L$ of 1.25 mm, a second radius of 0.4 mm, and a length $l_L$ of 7.0 mm. According to some embodiments, the dimensions of the tapered tube opening are selected for tuning the resonance frequency. In order to satisfy with the acoustic wave behavior in Helmholtz resonator, the range of the geometric parameters should be within about 10%. In FIG. 6, the walls of the tapered second tube opening 606 have a thickness of 1 mm. According to some embodiments, the walls of a tapered opening may range from about 1 mm to about 2 mm.

In FIG. 6, a moving element (i.e., liquid) 608 is disposed in cavity 604 of device 600. The liquid 608 has a thickness of 2 mm for a volume of about 100.5 mm$^3$. According to some embodiments, the thickness of a moving element in the cavity may range from about 2 mm to about 3 mm, and/or the volume of a moving element in the cavity may range from about 100.5 mm$^3$ to about 150.8 mm$^3$.

In FIG. 6, a mesh element (e.g., foam or metal) 610 is disposed in cavity 604 of device 600. The mesh 610 may be used to maintain the moving element 608 at a desired position in cavity 604. According to some embodiments, the thickness of a mesh element in the cavity may range from about 0.2 mm to about 0.5 mm, and/or the pore size of a mesh element in the cavity may range from about 0.1 mm to about 0.2 mm (e.g., 100 μm). In some embodiments, the mesh element is disposed in a device during assembly of the device. In other embodiments, the mesh element is disposed in a device after device assembly but prior to use of the device.

In some embodiments, the combination of a mesh and a liquid moving element create a liquid membrane for attenuating higher sound pressures. Due to surface tension, the liquid may form a meniscus in each pore of the mesh. The mesh and/or the cavity may be treated to further control the surface tension. According to some embodiments, more than one mesh element is included. For example, a cascade of mesh elements may be disposed in the cavity. A moving element like a liquid droplet may be disposed after each mesh such that sound waves must pass through a cascade of liquid membranes operating to attenuate the sound.

According to some embodiments, an inner surface shape, angle, or texture of a tapered second tube opening or nozzle may be varied to change the pressure field difference ΔP between the nozzle and the cavity of a device. The greater the pressure field difference ΔP, the more sound is absorbed/attenuated. Similarly, length of a tapered second tube opening or nozzle may be varied to change the frequencies transmitted.

According to some embodiments, more than one tapered second tube opening or nozzle (e.g., 3-7 tapered second tube openings and/or nozzles) may be included. For example, parallel nozzles may decrease insertion loss by matching background impedance. A plurality of nozzles may be arranged in one or more patterns.

Figure 7A:
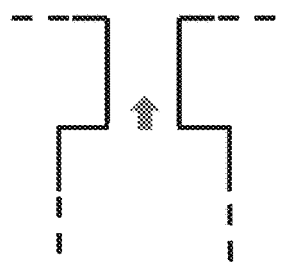
FIGS. 7A-7H are a series of schematic views of different nozzles and nozzle configurations in accordance with some embodiments.
Figure 7B:
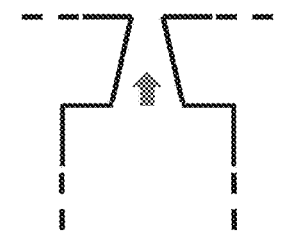
Figure 7C:
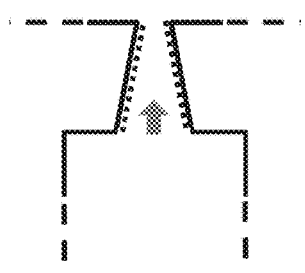
Figure 7D:
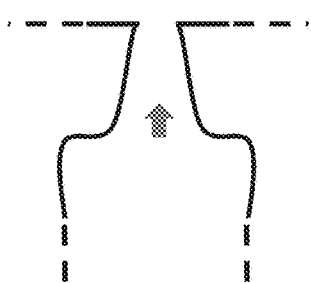
Figure 7E:
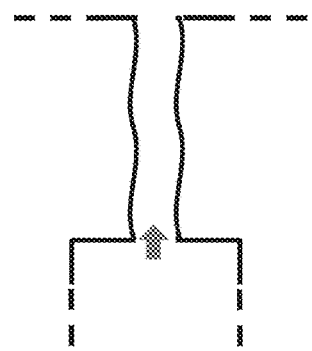
Figure 7F:
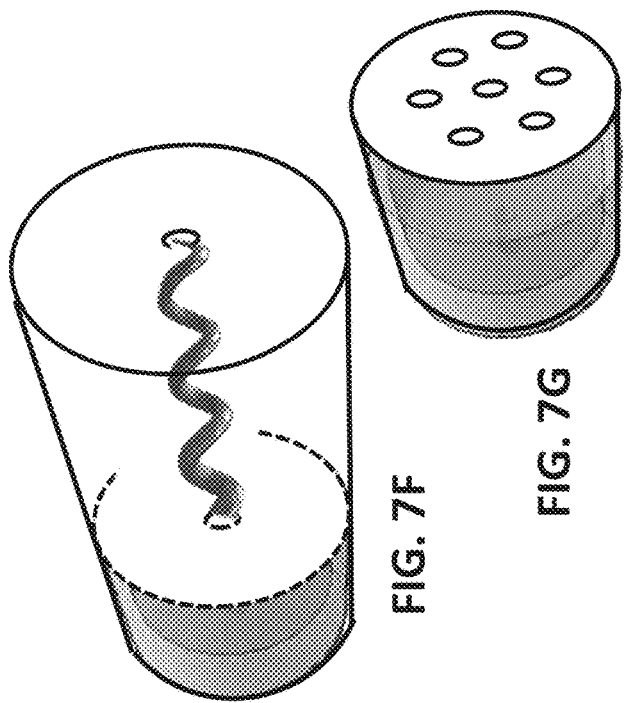
Figure 7G:
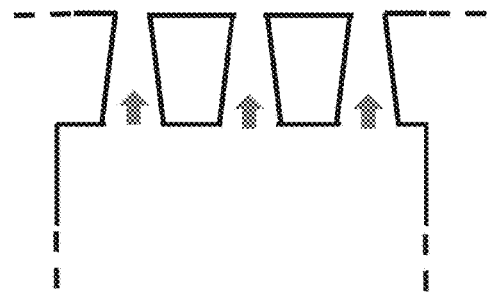
Figure 7H:
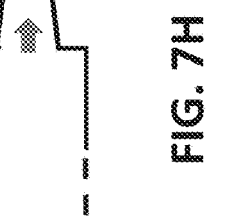

FIGS. 7A-7H are a series of schematic views of different nozzles and nozzle configurations in accordance with some embodiments. FIG. 7A illustrates a cross-section of a short nozzle with very little tapering for transmitting sound waves of greater amplitudes in a relatively small frequency range (e.g., about 100 Hz to about 800 Hz). FIG. 7B illustrates a cross-section of a short nozzle with a greater angle of tapering for attenuating sound waves of greater amplitudes. FIG. 7C illustrates a cross-section of a short nozzle with the same angle of tapering plus inner surface texture for additional absorption of sound. FIG. 7D illustrates a cross-section of a more conical nozzle for less insertion loss. FIG. 7E illustrates a cross-section of a longer nozzle for transmitting sound waves in a broader frequency range. Similarly, FIG. 7F illustrates a perspective cross-section of a device with a long helical nozzle for transmitting sound waves in a broader frequency range (e.g., about 50 Hz to about 4,000 Hz). FIG. 7G illustrates a perspective cross-section of a device with a plurality of nozzles for transmitting sound waves in a broader frequency range (e.g., about 50 Hz to about 4,000 Hz). FIG. 7H illustrates a cross-section of a series of parallel nozzles for less insertion loss.

EXAMPLES

Figure 8:
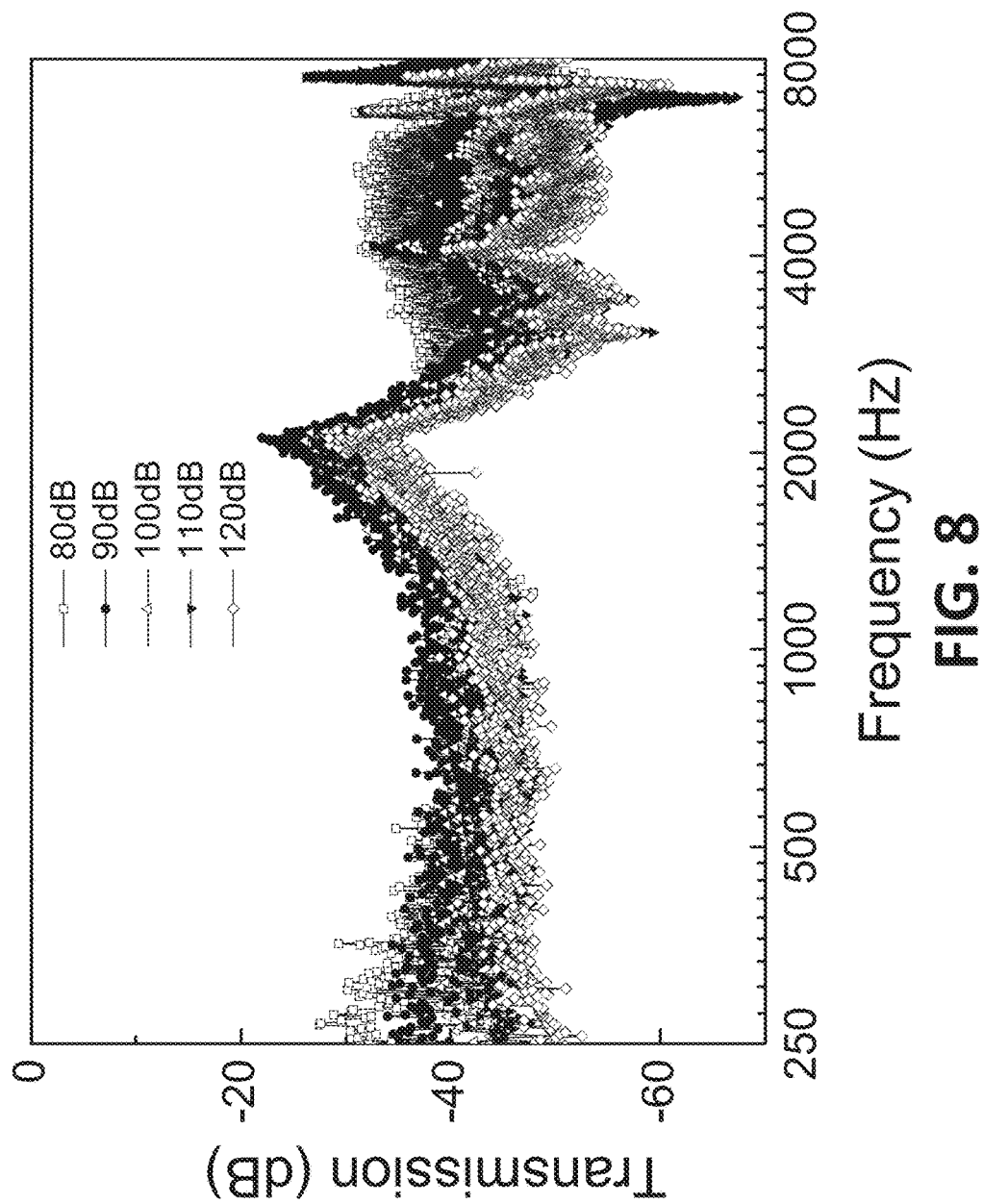
FIG. 8 is a plot illustrating transmission spectra of a sample from a hearing protection device without a droplet in accordance with some embodiments.
Figure 9:
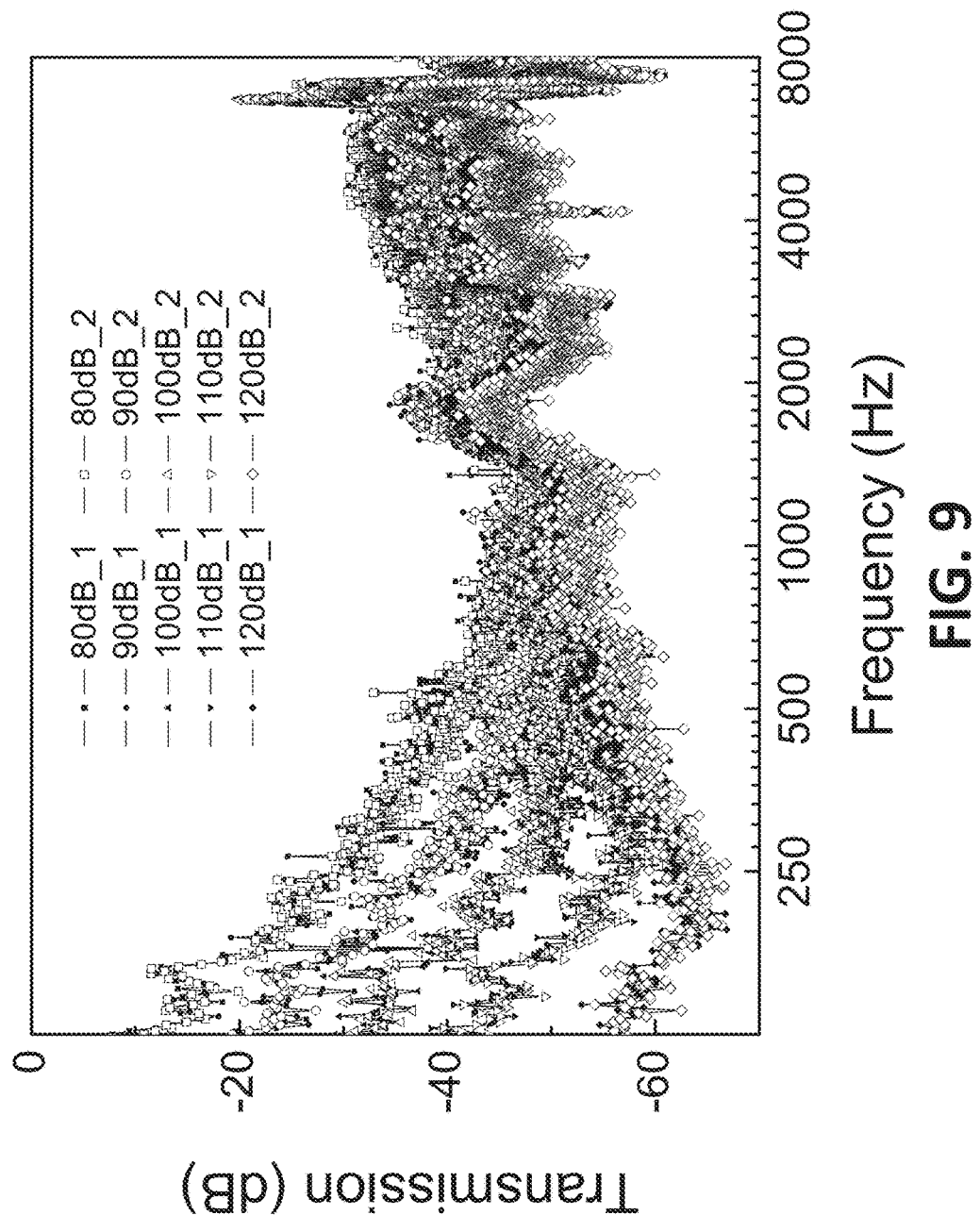
FIG. 9 is a plot illustrating transmission spectra of a sample from a hearing protection device with a droplet under different incident sound pressure levels in accordance with some embodiments.

A series of experiments were conducted using the prototype device depicted in FIG. 6 in accordance with some embodiments. First, the device was tested without a droplet under different incident sound pressure levels, including 80 dB, 90 dB, 100 dB, 110 dB, and 120 dB. A plot of the measured transmission spectra is shown in FIG. 8. In FIG. 8, a transmission peak around 2 kHz may be observed, and the transmission spectra almost overlap for the different incident sound pressure level. Next, the device was tested with a droplet under the different incident sound pressure levels. A plot of the measured transmission spectra is shown in FIG. 9. In FIG. 9, the transmission spectra show clear sound pressure level dependence when the droplet is injected into the cavity in the low frequency range. Due to the force balance of the droplet in the tapered channel—the higher incident pressure and more fluid in the channel—more energy is attenuated through the device. Therefore, the transmission coefficient drops with the increase of the incident sound pressure level. It is noted that the measurement sequence for the sound pressure level dependent experiment is: 80 dB_1; 90 dB_1; 100 dB_1; 110 dB_1; 120 dB_1; 80 dB_2; 90 dB_2; 100 dB_2; 110 dB_2; 120 dB_2. The transmission spectra for the same incident sound pressure level overlap with each other closely. Thus, the prototype device demonstrates good reversibility in accordance with some embodiments.

Figure 10:
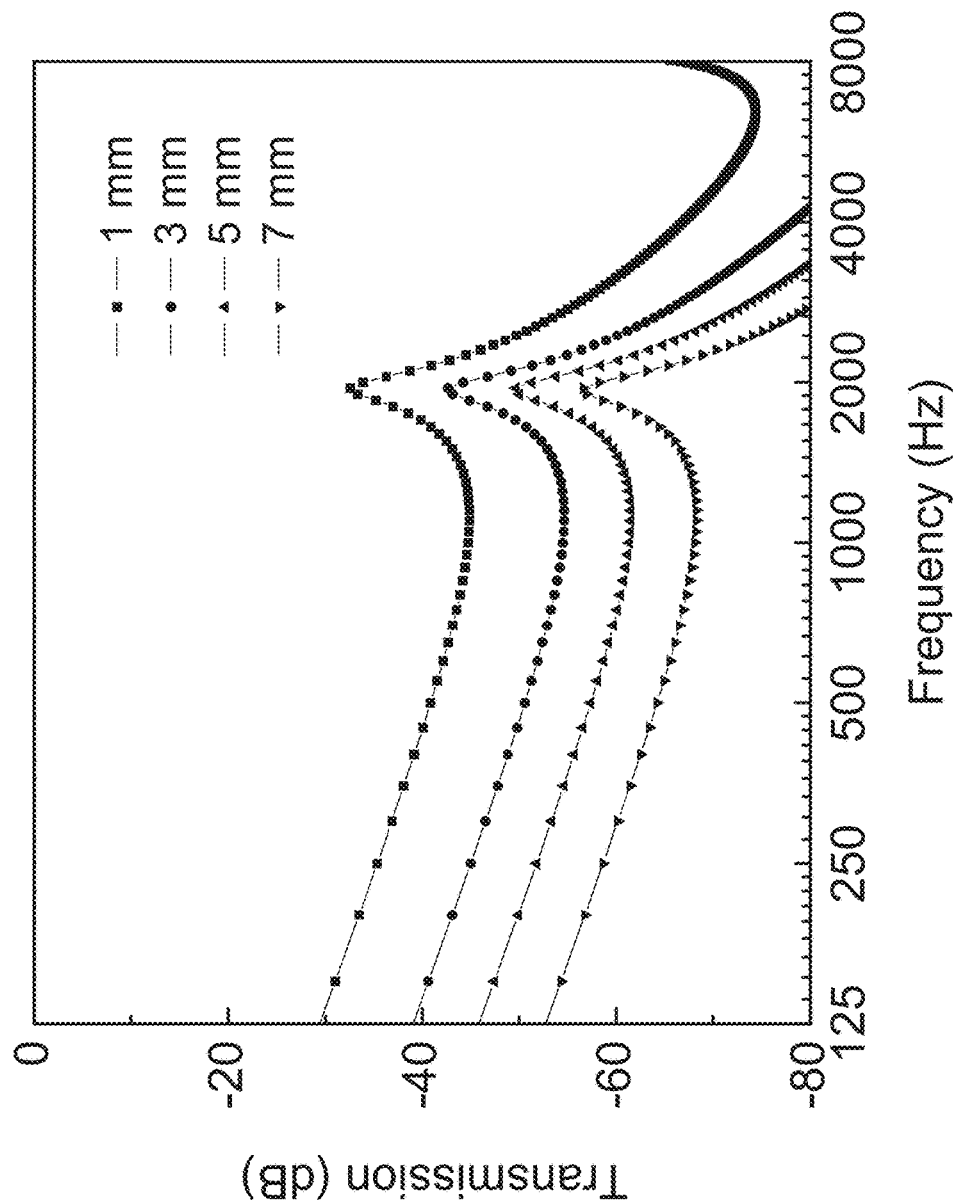
FIG. 10 is a plot illustrating transmission spectra simulated for the front end of the droplet at different positions in the tapered channel of a hearing protection device in accordance with some embodiments.

In addition, FIG. 10 is a plot illustrating transmission spectra simulated for the front end of the droplet at different positions in the tapered channel of the device in accordance with some embodiments. The numerical simulation results in FIG. 10 show a similar trend of the transmission for the droplet front end at different positions, demonstrating that the device performs under different sound pressure levels.

In some embodiments, systems, apparatus, and methods may be used to attenuate acoustic energy over a broad range of frequencies. More applications may be addressed and/or improved with smaller apparatus and systems. For example, a device with the disclosed features may be as small as few centimeters due to the enhanced acoustic wave interaction with the acoustic metamaterials. The sound pressure level sensitive capability may be realized in a passive design, thus requiring no additional power supply.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A hearing protection device having an outer shape and size for inserting at least a portion of the device in a human ear canal, the outer shape defining a first opening for receiving incident acoustic energy from an environment and a second opening positioned opposite to the first opening for transmitting filtered acoustic energy into the ear canal, the device having a longitudinal axis extending from the first opening to the second opening, the device further defining:
   a first conduit extending inward from the first opening;
   a cavity in fluid communication with the first conduit, the cavity for selectively amplifying and/or dampening the acoustic energy based on a resonance frequency of the cavity, the cavity further comprising:
      a mesh element disposed in a plane substantially normal to the longitudinal axis, the mesh element dividing the cavity into a proximal compartment for receiving the acoustic energy from the first conduit and a distal compartment; and
      liquid disposed in the distal compartment, wherein no significant amount of the liquid is present in the proximal compartment, the liquid displaceable relative to the device in a direction substantially aligned with the longitudinal axis; and a second conduit in fluid communication with the distal compartment and extending outward to the second opening, the second conduit being tapered towards the second opening and for receiving a portion of the displaced liquid in response to a sound pressure level of the acoustic energy, an extent of displacement of the liquid into the second conduit based on the sound pressure level of the acoustic energy, wherein the second conduit selectively attenuates acoustic energy from the cavity based on the extent of displacement of the liquid into the second conduit.

2. The hearing protection device of claim 1, wherein the device is configured to be combined with an ear plug.

3. The hearing protection device of claim 1, wherein the outer shape comprises at least one of a domed flange, a bell-shape, and a bullet-shape.

4. The hearing protection device of claim 1, wherein the device comprises at least one of a foam, a silicone, and a thermoplastic.

5. The hearing protection device of claim 1, wherein the device is manufactured using at least one of additive manufacturing, rotational plastic molding, injection molding, blow molding, extrusion molding, and thermoforming.

6. The hearing protection device of claim 1, wherein the device has an outer radius from about 5 mm to about 7 mm and an outer length from about 10 mm to about 14 mm.

7. The hearing protection device of claim 1, wherein the mesh element comprises at least one of a foam and a metal.

8. The hearing protection device of claim 1, wherein the mesh element has a thickness from about 0.2 mm to about 0.5 mm.

9. The hearing protection device of claim 1, wherein the mesh element has a pore size from about 0.1 mm to about 0.2 mm.

10. The hearing protection device of claim 1, wherein a mesh element maintains the liquid at a particular position in the cavity.

11. The hearing protection device of claim 1, wherein the position of the liquid is based at least in part on at least one of:
   an acoustic pressure field difference between the cavity and the second conduit; and
   a surface tension between the liquid and at least one of the mesh element, air, an inner surface of the cavity, and an inner surface of the second conduit.

12. The hearing protection device of claim 11, wherein at least one of the mesh element, the inner surface of the cavity, and the inner surface of the second conduit is treated to control the surface tension.

13. The hearing protection device of claim 11, wherein at least one of a shape, an angle, and a texture of the inner surface of the second conduit is selected to modify the acoustic pressure field difference between the cavity and the second conduit.

14. The hearing protection device of claim 1, wherein a length of the second conduit is selected to modify frequencies transmitted of the filtered acoustic energy.

15. The hearing protection device of claim 14, wherein the length of the second conduit is selected to allow transmission of frequencies from about 50 Hz to about 4,000 Hz.

16. The hearing protection device of claim 14, wherein the length of the second conduit is selected to allow transmission of frequencies from about 100 Hz to about 800 Hz.

17. The hearing protection device of claim 1, wherein the mesh element and the liquid form a liquid membrane.

18. The hearing protection device of claim 1, wherein the liquid forms a meniscus in each of a plurality of pores of the mesh element for a plurality of menisci.

19. The hearing protection device of claim 1, wherein the mesh element comprises a cascade of mesh elements disposed in a plurality of parallel planes, each plane of the plurality of planes being substantially normal to the longitudinal axis, the cascade of mesh elements dividing the cavity into more than two compartments.

20. The hearing protection device of claim 19, wherein liquid is disposed in at least one intermediate compartment between a first mesh element and a second mesh element of the cascade of mesh elements such that the liquid forms a meniscus in each of a plurality of pores of the first mesh element and each of a plurality of pores of the second mesh element.

21. A method for protecting hearing of a listener in an environment, the method comprising:
   inserting at least a portion of a device in a human ear canal, the device having an outer shape defining a first opening for receiving incident acoustic energy from the environment and a second opening positioned opposite to the first opening for transmitting filtered acoustic energy into the ear canal, the device having a longitudinal axis extending from the first opening to the second opening;
   receiving incident acoustic energy from the environment via the first opening in the device, a first conduit extending inward from the first opening;
   selectively amplifying and/or dampening the acoustic energy via a cavity in fluid communication with the first conduit based on a resonance frequency of the cavity, the cavity further comprising a mesh element disposed in a plane substantially normal to the longitudinal axis, the mesh element dividing the cavity into a proximal compartment for receiving the acoustic energy from the first conduit and a distal compartment;
   selectively attenuating, based on a sound pressure level of acoustic energy in the cavity, acoustic energy from the cavity via liquid disposed in the distal compartment and a second conduit in fluid communication with the distal compartment and extending outward to the second opening, the liquid displaceable relative to the device in a direction substantially aligned with the longitudinal axis, the second conduit being tapered towards the second opening and receiving a portion of the displaced liquid in response to a sound pressure level of the acoustic energy, an extent of displacement of the liquid into the second conduit based on the sound pressure level of the acoustic energy, wherein no significant amount of the liquid is present in the proximal compartment, and wherein the second conduit selectively attenuates the acoustic energy based on the extend of displacement of the liquid into the second conduit; and
   transmitting the filtered acoustic energy via the second opening of the second conduit positioned opposite to the first opening along the longitudinal axis.

22. An apparatus for filtering acoustic energy in an environment, the apparatus comprising:
   a first conduit substantially aligned with a longitudinal axis, the first conduit defining a first opening for receiving incident acoustic energy from the environment;
   a cavity in fluid communication with the first conduit, the cavity for selectively amplifying and/or dampening the acoustic energy based on a resonance frequency of the cavity, the cavity comprising a moving element disposed in a distal compartment of the cavity and not being present in a proximal compartment of the cavity, the moving element displaceable relative to the apparatus in a direction substantially aligned with the longitudinal axis; and a second conduit substantially aligned with the longitudinal axis and in fluid communication with the cavity, the second conduit being tapered towards a second opening and for receiving a portion of the displaced moving element in response to a sound pressure level of the acoustic energy, an extent of displacement of the moving element into the second conduit based on the sound pressure level of the acoustic energy, the second conduit further for selectively attenuating acoustic energy from the cavity based on the extent of displacement of the moving element into the second conduit, the second opening positioned opposite to the first opening along the longitudinal axis for transmitting filtered acoustic energy.

23. A method for filtering acoustic energy in an environment, the method comprising:

receiving incident acoustic energy from the environment via the first opening of a first conduit substantially aligned with a longitudinal axis;

selectively amplifying and/or dampening the acoustic energy via a cavity in fluid communication with the first conduit based on a resonance frequency of the cavity, the cavity comprising a moving element disposed in a distal compartment of the cavity and not being present in a proximal compartment of the cavity, the moving element displaceable in a direction substantially aligned with the longitudinal axis;

selectively attenuating acoustic energy from the cavity via a second conduit substantially aligned with the longitudinal axis and in fluid communication with the cavity, the second conduit being tapered towards a second opening and for receiving a portion of the displaced moving element in response to a sound pressure level of the acoustic energy, an extent of displacement of the moving element into the second conduit based on the sound pressure level of the acoustic energy, wherein the second conduit selectively attenuates the acoustic energy based on the extend of displacement of the liquid into the second conduit; and transmitting filtered acoustic energy via a second opening defined by the second conduit and positioned opposite to the first opening along the longitudinal axis.

* * * * *